(12) United States Patent
Vanden Bussche et al.

(10) Patent No.: US 7,422,676 B2
(45) Date of Patent: Sep. 9, 2008

(54) APPARATUS AND PROCESS FOR THE SYNTHESIS OF HYDROGEN PEROXIDE DIRECTLY FROM HYDROGEN AND OXYGEN

(75) Inventors: Kurt M. Vanden Bussche, Lake in the Hills, IL (US); Anil R. Oroskar, Oakbrook, IL (US); Jeffery C. Bricker, Buffalo Grove, IL (US); Laszlo T. Nemeth, Barrington, IL (US); Gavin P. Towler, Barrington, IL (US)

(73) Assignee: UOP LLC, Des Plaines, IL (US)

( * ) Notice: Subject to any disclaimer, the term of this patent is extended or adjusted under 35 U.S.C. 154(b) by 297 days.

(21) Appl. No.: 11/313,201

(22) Filed: Dec. 20, 2005

(65) Prior Publication Data

US 2006/0096869 A1    May 11, 2006

Related U.S. Application Data

(60) Division of application No. 10/309,725, filed on Dec. 4, 2002, now Pat. No. 7,115,192, which is a continuation-in-part of application No. 09/850,438, filed on May 7, 2001, now Pat. No. 6,713,036.

(51) Int. Cl.
*C25B 1/30* (2006.01)
*C25B 1/04* (2006.01)
*C01B 15/029* (2006.01)

(52) U.S. Cl. ............... 205/628; 423/584; 205/466
(58) Field of Classification Search .......... None
See application file for complete search history.

(56) References Cited

U.S. PATENT DOCUMENTS

| 4,007,256 | A | 2/1977 | Kim et al. ............... 423/584 |
| 4,284,899 | A | 8/1981 | Bendiks ............... 290/1 |
| 4,336,240 | A | 6/1982 | Moseley et al. ............... 423/584 |
| 4,347,231 | A | 8/1982 | Michaelson ............... 423/584 |
| 4,461,742 | A | 7/1984 | Rowe et al. ............... 422/129 |
| 4,488,951 | A | 12/1984 | Nolan et al. ............... 204/129 |
| 4,521,117 | A | 6/1985 | Ouwerkerk et al. ......... 366/165 |
| 4,832,938 | A | 5/1989 | Gosser et al. ............... 423/584 |
| 4,862,836 | A | 9/1989 | Chen et al. ............... 123/3 |
| 5,082,647 | A | 1/1992 | Chuang ............... 423/584 |
| 5,925,588 | A | 7/1999 | Chuang et al. ............... 502/181 |
| 6,004,517 | A | 12/1999 | Tirtowidjojo et al. ....... 422/129 |
| 6,036,827 | A | 3/2000 | Andrews et al. ............... 204/252 |
| 6,042,804 | A | 3/2000 | Huckins ............... 423/584 |
| 6,210,651 | B1 | 4/2001 | Nyström et al. ............... 423/584 |
| 6,655,829 | B1 | 12/2003 | Vanden Bussche et al. ....... 366/165.1 |
| 6,713,036 | B1 | 3/2004 | Vanden Bussche et al. .. 423/584 |
| 6,872,377 | B2 | 3/2005 | Fischer et al. ............... 423/584 |

OTHER PUBLICATIONS

*Microreactors, New Technology for Modern Chemistry*, by W. Ehrfedl, V. Hessel, H. Löwe, Wiley-VCH 2000, pp. 41-85.
*Microreaction technology: industrial prospects; proceedings of the Third International Conference on Microreaction Technology/IMRET2* by T.M. Floyd et al., W. Ehrfeld, Springer 2000, pp. 171-179.

*Primary Examiner*—Harry D Wilkins, III
(74) *Attorney, Agent, or Firm*—Arthur E. Gooding

(57) ABSTRACT

A device is disclosed for the generation of hydrogen peroxide. The device produces hydrogen peroxide on an as-needed basis through the use of electrolysis of water, remixing hydrogen and oxygen in an appropriate ratio, and reacting the hydrogen and oxygen in water in a reactor.

11 Claims, 2 Drawing Sheets

US 7,422,676 B2

APPARATUS AND PROCESS FOR THE SYNTHESIS OF HYDROGEN PEROXIDE DIRECTLY FROM HYDROGEN AND OXYGEN

CROSS-REFERENCE TO RELATED APPLICATIONS

This application is a Division of application Ser. No. 10/309,725,filed Dec. 4, 2002, now U.S. Pat. No. 7,115,192 which in turn is a Continuation-In-Part of application Ser. No. 09/850,438 filed May 7, 2001, now U.S. Pat. No. 6,713,036, the contents of which are hereby incorporated by reference in their entirety.

FIELD OF THE INVENTION

The present invention relates to a device for producing hydrogen peroxide directly from hydrogen and oxygen, and a process for producing hydrogen peroxide.

BACKGROUND OF THE INVENTION

Currently the most widely practiced industrial scale production method for hydrogen peroxide is an indirect reaction of hydrogen and oxygen employing alkylanthraquinone as the working material. In a first catalytic hydrogenation step, the alkylanthraquinone, dissolved in a working solution comprising organic solvents (e.g. di-isobutylcarbinol and methyl naphthalene), is converted to alkylanthrahydroquinone. In a separate autooxidation step, this reduced compound is oxidized to regenerate the alkylanthraquinone and yield hydrogen peroxide. Subsequent separation by aqueous extraction, refining, and concentration operations are then employed to give a merchant grade product.

Overall, this indirect route to $H_2O_2$ formation, whereby a carrier medium is reduced and then oxidized, adds complexity and requires high installation and operating costs. One notable drawback is the significant solubility of the alkylanthraquinone in the aqueous extraction medium used to separate the hydrogen peroxide product. This promotes loss of working solution and leads to contamination of the hydrogen peroxide product with organic species that, when the hydrogen peroxide is concentrated to levels suitable for transport, are reactive with it. A second problem relates to the solubility of the aqueous extraction solution in the alkylanthraquinone working solution. When wet working solution is separated from the aqueous phase for recycle to the indirect oxidation stage, residual aqueous phase "pockets" within the organic solution provide regions for hydrogen peroxide product to concentrate to the extent of becoming hazardous. A third problem relates to the usage and recovery of an organic compound when small amounts of hydrogen peroxide are needed without the organic contamination in an aqueous stream.

Considerably more simple and economical than the alkylanthraquinone route is the direct synthesis of hydrogen peroxide from gaseous hydrogen and oxygen feed streams. This process is disclosed in U.S. Pat. No. 4,832,938 B1 and other references, but attempts at commercialization have led to industrial accidents resulting from the inherent explosion hazards of this process. Namely, explosive concentrations of hydrogen in an oxygen-hydrogen gaseous mixture at normal temperature and pressure are from 4.7-93.9% by volume. Thus the range is extremely broad.

It is also known that dilution of the gaseous mixture with an inert gas like nitrogen scarcely changes the lower limit concentrations, on an inert gas-free basis, of the two gases. Within normal ranges of pressure variation (1-200 atmospheres) and temperature variation (0-100° C.) the explosive range is known to undergo little change. Furthermore, even when these reactants are brought together in a ratio that, in the homogeneous condition, would be outside the flammability envelope, the establishment of homogeneity from pure components necessarily involves at least a temporary passage through the flammability envelope. For these reasons, the explosion risks associated with the direct contacting of hydrogen and oxygen are not easily mitigated.

In the area of directly contacting hydrogen and oxygen, some efforts have also been made to contain the reaction in a liquid phase. For example, U.S. Pat. No. 5,925,588 B1 discloses the use of a catalyst having a modified hydrophobic/hydrophilic support to provide optimum performance in an aqueous liquid phase. Also, U.S. Pat. No. 6,042,804 B1 discloses dispersing minute bubbles of hydrogen and oxygen into a rapidly flowing acidic aqueous liquid medium containing a catalyst. Unfortunately, however, the hydrogen and oxygen reactants are only slightly soluble in the aqueous reaction solvents disclosed in these references.

Other references, namely U.S. Pat. No. 4,336,240 B1 and U.S. Pat. No. 4,347,231 B1 disclose two-phase reaction systems with a homogeneous catalyst dissolved in an organic phase. As mentioned in the former of these two references, homogeneous catalyst systems in general suffer from drawbacks that are a deterrent to their commercial use. The adverse characteristics include poor catalyst stability under reaction conditions, limited catalyst solubility in the reaction medium, and low reaction rates for the production of hydrogen peroxide. In addition, a gaseous $H_2/O_2$ containing environment above the two-phase liquid reaction system maintains the equilibrium concentrations of these reactants dissolved in the liquid phase. Therefore, this gaseous atmosphere above the reaction liquid must necessarily be outside the flammability envelope, thus greatly restricting the range of potential reactant mole ratios in the liquid phase.

It would be useful to have a device and process for making hydrogen peroxide in a convenient manner, on an as-needed basis, without the need of extra chemicals, and without generating a waste product stream.

SUMMARY OF THE INVENTION

The present invention is an apparatus for generating a hydrogen peroxide solution for use in appliances, or for intermittent usage in the application of a bleaching agent. The apparatus includes an electrolyzer and a reactor in fluid communication with the electrolyzer. The apparatus has a source of water, where the electrolyzer dissociates the water into hydrogen and oxygen. The gases and water are reacted in a reactor to form hydrogen peroxide.

In one embodiment, the apparatus includes an air inlet port for increasing the ratio of oxygen to hydrogen in the gas mixture coming from the mixing unit. This provides for improved composition of the gas mixture to improve the concentration of hydrogen peroxide in water.

In an alternate embodiment, the invention comprises an electrolyzer and a reactor. The electrolyzer generates hydrogen and oxygen gases, and the gases are directed to the reactor. The reactor has a water inlet port for adding water to the reactor where the water flows over a solid catalyst on a substrate. The gases enter the reactor through at least one gas inlet port and dissolve in the water. The dissolved hydrogen is oxidized to form hydrogen peroxide. The reactor, optionally, has an inlet port for adding supplemental air to the reactor. The supplemental air provides for control of the oxygen to hydrogen ratio.

Other objects, advantages and applications of the present invention will become apparent to those skilled in the art from the following detailed description.

DETAILED DESCRIPTION OF THE INVENTION

There are numerous applications where a bleaching agent is helpful, such as, for example the removal of stains and the use of bleach for disinfecting. Conventionally, the use of bleach in an environment such as a personal residence requires the purchase of the bleach. The bleach must be stored in a container, and the user must be aware of the amount on hand available for use. The bleach can also be used for disinfectant purposes, such as a periodic application of bleach to a garbage disposal. The use in a garbage disposal can remove bacteria that are creating unpleasant odors as a result of growth in the garbage disposal. One such bleaching agent is hydrogen peroxide. However, hydrogen peroxide requires storage in a suitable container to prevent breakdown from UV light, such as using a brown plastic container. Hydrogen peroxide also will degrade over time, rendering a solution ineffective if allowed to sit for to long a time.

Figure 1:
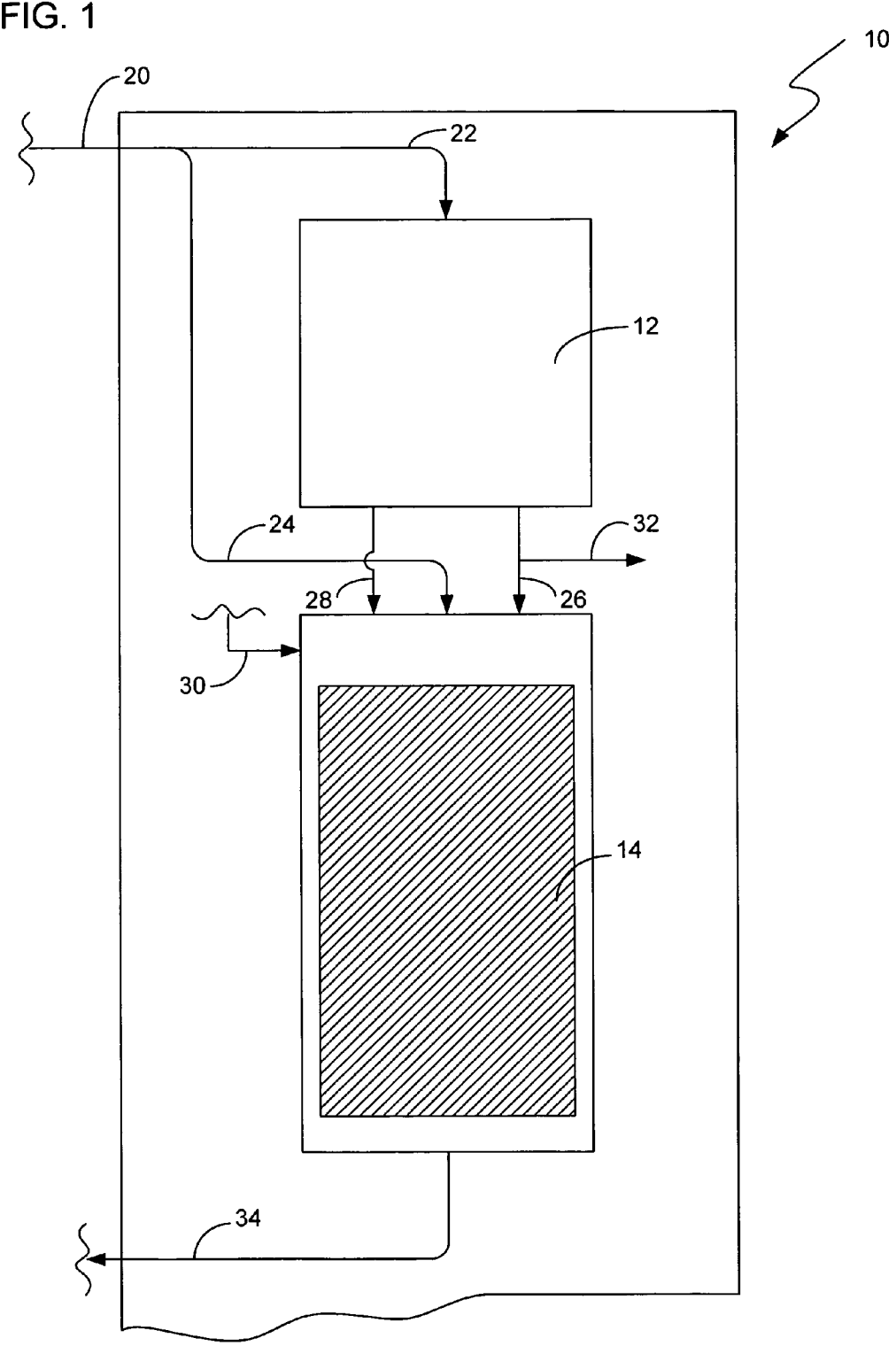
FIG. 1 is a diagram of an apparatus of the present invention.

The present invention provides for the production of an aqueous hydrogen peroxide solution in-line or as a parallel stream to a regular water line. The solution is produced on an as-needed basis without the need to add chemicals when affixed to a water pipe. The invention includes an electrolyzer for dissociating water directed from a water line. The gases produced from the electrolyzer, hydrogen and oxygen, are directed to a reactor in fluid communication with the electrolyzer with water flowing over an appropriate catalyst for the oxidation of hydrogen to hydrogen peroxide. FIG. 1 is a diagram of the present invention. A self contained hydrogen peroxide unit 10 of the present invention includes an electrolyzer 12 and a hydrogen peroxide reactor 14. The hydrogen peroxide unit 10 has an inlet 20 for water. The water is split into two conduits 22 and 24, where one conduit 22 is directed to the electrolyzer 12, and the second conduit 24 is directed to the reactor 14. The electrolyzer 12 dissociates the water into hydrogen and oxygen gases. Hydrogen is directed through one conduit 26 to the reactor 14, and oxygen is directed through a second conduit 28 to the reactor 14. Additional oxygen, usually in the form of air, is directed to the reactor 14 through an independent air inlet 30. In an alternate design, the hydrogen conduit 26 includes a conduit 32 for diverting some of the hydrogen produced. This diversion can use the hydrogen for combustion to provide heat either to the unit 10 or an auxiliary device. The reactor 14 includes an outlet port for directing a hydrogen peroxide solution through a product conduit 34. The product conduit 34 directs the hydrogen peroxide solution to a desired destination. A desired destination can be directing the hydrogen peroxide solution for use as a bleaching agent, as an antiseptic agent, or as a disinfectant agent, or to a device that will use a bleaching or disinfectant agent.

Figure 2:
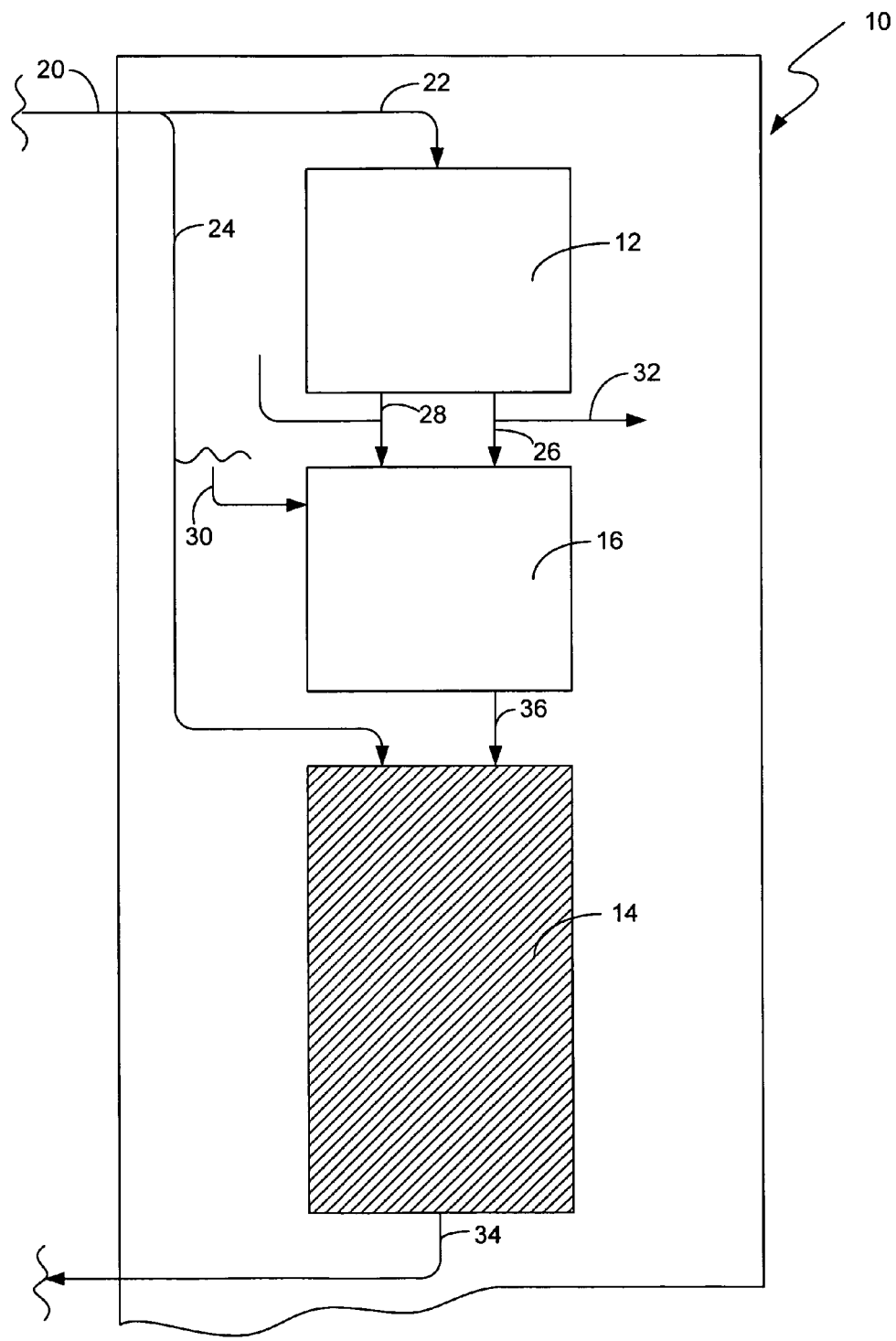
FIG. 2 is an alternate diagram of an apparatus of the present invention.

In an alternate embodiment, the invention includes a mixer for mixing the hydrogen and oxygen into a gas mixture before directing the gas mixture to the reactor, as shown in FIG. 2. The hydrogen peroxide unit 10 includes an electrolyzer 12, a mixer 16 for creating a hydrogen/oxygen mixture, and a hydrogen peroxide reactor 14. The unit 10 has an inlet 20 for water. The inlet 20 splits into two conduits 22 and 24, where one conduit 22 directs water to the electrolyzer 12, and the second conduit 24 directs water to the reactor 14. The electrolyzer 12 generates hydrogen and oxygen as gases. The electrolyzer 12 has a conduit 26 for hydrogen and a conduit 28 for oxygen. The mixer includes inlet ports for the hydrogen and oxygen. The hydrogen conduits 26 is in fluid communication with the hydrogen inlet port, and the oxygen conduit 28 is in fluid communication with the oxygen inlet port. Optionally, the mixer 16 includes at least one inlet port 30 for the addition of oxygen to the hydrogen and oxygen to increase the ratio of oxygen to hydrogen in the mixer 16. The inlet port for oxygen can alternately be used as an inlet port for air to achieve the increase in oxygen to hydrogen ratio. The mixer 16 includes an outlet port 36 in fluid communication with the reactor 14. The outlet port 36 carries the hydrogen/oxygen mixture to the reactor 14. The reactor 14 includes a product outlet port in fluid communication with a product conduit 34 for directing the hydrogen peroxide solution to a desired destination. Alternately, the unit 10 includes a conduit 32 for diverting some of the hydrogen produced from the electrolyzer 12 to an alternate destination.

The electrolyzer:

The electrolyzer is a convenient device for using ordinary tap water and converting a portion of the tap water into hydrogen and oxygen gases through the application of energy. A preferred embodiment includes an electrolyzer using electrical power. The use of an electrolyzer is a convenient method and device for generating the reactants, hydrogen and oxygen, as needed. There is no need to provide other chemicals, or provide for storage of the reactants, and therefore there is no waste of the hydrogen peroxide produced.

The electrolyzer used for water splitting is a clean method of producing hydrogen, but is more expensive than heat. The standard free energy, enthalpy, and entropy of water are, respectively, G=237.19 kJ/mol (56.69 kcal/mol), H=285.85 kJ/mol (68.32 kcal/mol), and S=70.08 J/(mol·K) (16.72 cal/(mol·K)). The value for the free energy is equivalent to an electromotive force of 1.23 V, which is the minimum voltage needed to get the reaction to proceed at conditions of standard temperature and pressure. The total energy required for the reaction to proceed is the enthalpy, and can be a combination of electrical energy and heat. Because G=H−T·S and S is positive, the electrical work needed (G) can be reduced by operating at higher temperatures. This is a shifting of the energy load from electrical energy to heat with increasing operating temperatures. This is desirable because the production of heat is generally less expensive than electricity.

The electrolyzer has a cell wherein water is admitted. Within the cell are two electrodes having different polarities, and current can flow from one electrode to the other through the water within the cell. Also within the cell, the electrodes are separated by a membrane permeable to an aqueous solution, to prevent the mixing of the hydrogen and oxygen gases generated. When electrical current is passing through the cell, the water is decomposed and hydrogen is generated at one electrode and oxygen is generated at the other electrode. The electrolyzer can employ one of three types of processes: an aqueous alkaline system; a solid polymer electrolyte (SPE); or a high temperature steam electrolysis with temperatures in the range of about 700° C. to about 1000° C.

The aqueous alkaline system is a traditional process and employs an ionic compound added to the water to improve the conductivity through the cell. The aqueous electrolyte systems typically employ a barrier porous to the liquid phase but blocking gas generated at the electrodes which enables the collection of the oxygen and hydrogen gases separately and prevents mixing. The electrolyzer can be a tank type or a filter press type. The tank type has a plurality of individual cells connected in parallel. This permits the use of one power source using low voltage. The current necessary is proportional to the number of cells, and in turn the transformers and rectifiers are sized accordingly. The filter press type has a plurality of cells connected in series. This is called a bipolar arrangement and the voltage required is proportional to the number of cells for the unit. The units are run at a pressure from about 100 kPa (0 psig) to about 600 kPa (72.4 psig). Running at higher pressure allows for smaller lines and is an efficient method of compressing the gases. The electrolyzer is operated at a temperature from about 0° C. to about 60° C., and preferably from about 25° C. to about 40° C. Heating the water reduces some of the electrolyzer power requirements. A typical ionic compound used in the cell is potassium hydroxide, KOH.

An alternate electrolyzer uses a solid polymer electrolyte (SPE) for improving the conductivity through the cell. An example of a solid polymer electrolyte useable in an electrolyzer is a polysulfonated fluoroionomer. Polysulfonated fluoroionomers are available commercially, for example, NAFION™ is made by E. I. Dupont in Wilmington, Del. Electrolyzers using an SPE in the form of a polymer sheet have the electrodes in electrical contact with the polymer sheet. The hydrogen ion ($H^+$) is produced at the anode and migrates through the SPE to the cathode to produce $H_2$. The hydroxyl ions ($OH^-$) produce oxygen at the anode. These units have low internal resistance and can operate at higher temperatures than the aqueous alkaline units.

For practical usage, the electrodes are separated to direct the different generated gases into separate receiving devices. The gases are collected, and each gas is separately directed to the mixer for mixing to form a stable mixture to be reacted upon contact with the catalyst. Each gas enters at least one inlet port to the mixer, wherein the gases are mixed and the mixture is directed to an outlet port in fluid communication with the conduit supply end. The appropriate ratio of oxygen to hydrogen is made by either adding additional oxygen from air, or by diverting some of the hydrogen for an alternate use.

The reason for decomposing water for later reaction is that electrolysis is a safe and convenient way for generating hydrogen in relatively small amounts as needed. The hydrogen is then reacted with oxygen to produce hydrogen peroxide in water with no other products.

The volume of gases to be reacted is easily controlled by the amount of electrical power supplied to the electrolyzer. Details of an electrolyzer are well known in the art, as demonstrated in U.S. Pat. No. 6,036,827, and which is incorporated by reference in its entirety. The electrical power supplied to the electrolyzer is of sufficient quantity to dissociate water at a rate between 0.01 milligrams/min. to about 10 grams/min. Optionally, a control system is incorporated in the electrolyzer to provide an upper limit on the amount of electrical power used by the electrolyzer, including, but not limited to, a fuse for shutting off power to the electrolyzer.

When the water used in the electrolyzer is from a source of hard water, the water will need to be softened first. The hardness, especially the iron ion content will have an adverse effect on the operation of the electrolyzer.

The mixer:

The gases from the electrolyzer are mixed in a mixer. The mixer has at least one first supply tube having a first supply tube receiving end for receiving a first fluid stream and a discharge end opposite the receiving end; at least one second supply tube having a second supply tube receiving end for receiving a first fluid stream and a discharge end opposite the receiving end; a mixing chamber in fluid communication with the first and second supply tube discharge ends; and a mixing chamber outlet for discharging a mixed stream of the first and second fluid streams from the mixing chamber.

In a preferred embodiment of the mixer, the mixing chamber of the mixer is in fluid communication with a plurality of first supply tubes discharge ends, and in fluid communication with a plurality of second ends. The first and second supply tube discharge ends are arrayed in an interdigitated pattern on the mixing chamber. This provides for a layering of the gases upon entry to the mixing chamber and rapid diffusional mixing within the chamber.

The mixer can be any type of mixer for mixing gases. However, the constraints on the mixer are that mixing chambers and channels need to be sized to keep the volumes of mixtures of hydrogen and oxygen below cell sizes wherein ignition and propagation of a combustion reaction between hydrogen and oxygen. In a preferred embodiment of the mixer described above, the discharge ends of the supply tubes have an inner diameter of less than 0.02 cm. and the mixing chamber has an inner diameter of less than 0.02 cm.

Another possible mixer design includes a packed bed. The mixer has a plurality of supply tube discharge ends in fluid communication with the mixing chamber. The mixing chamber is a packed bed of inert material providing a series of intertwined channels having channel diameters of less than 0.02 cm.

One possible mixer design includes a mixing unit, as described in U.S. patent application Ser. No. 09/850,470, filed on May 7, 2001, which is incorporated by reference in its entirety. The mixing unit provides a mixing chamber with a plurality of supply tubes arranged about the mixing chamber perimeter. The supply tubes open into the mixing chamber in such a manner that particular fluids introduced at defined flow rates will form a fluid spiral flowing concentrically inward. This vortex formation extends the fluid residence time within the mixing chamber considerably, thereby improving mixing characteristics. Establishment of the desired helical and inward fluid flow path is primarily a function of both the angle of fluid introduction into the mixing chamber and the fluid kinetic energy. Fluids introduced radially, or, in the case of a cylindrical mixing chamber, directly toward its center, will not assume a helical flow path unless acted upon by another fluid with sufficient kinetic energy in the tangential direction. The present mixer achieves exceptional mixing by introducing the first and second fluids to be mixed both tangentially and radially. In one embodiment, the tangential fluid kinetic energy components are adequate to bend the radial flow components so that they assume the overall helical flow pattern with a sufficient number of windings to allow effective mixing. Since one fluid is introduced tangentially and another radially, it is preferred that the ratio of fluid kinetic energy of the tangentially flowing fluid to that of the radially flowing is greater than about 0.5 to provide the desired helical and inward flow pattern. The supply tubes can include additional tubes for the addition of air to the mixture to control the ratio of oxygen to hydrogen in the gas mixture. The mixing chamber is sized to be less than about 0.02 cm. in internal diameter.

The reactor:

The reactor 14 in the present invention is preferably a trickle bed reactor. The reactor comprises at least one inlet port for admitting hydrogen and oxygen to the reactor. The inlet port can provide for admitting water to the reactor, or in an alternative, a separate inlet port is provided for admitting water to the reactor. The reactor includes a chamber for holding a catalyst on a support material, referred to as the catalyst bed. In the reactor, water flows over the catalyst bed with a sufficient volume to form a liquid layer over the surface of the catalyst. The hydrogen and oxygen flow through the reactor and dissolve in the aqueous phase. The hydrogen in solution is oxidized on the surface of the catalyst bed to form hydrogen peroxide in the aqueous phase. The aqueous solution of hydrogen peroxide exits the reactor 14 through an outlet port. The outlet port is in fluid communication with a conduit 34 for directing the hydrogen peroxide solution to a desired destination. A desired destination can be as stated above. The reactor is sized to produce a hydrogen peroxide solution of less than about 5 mol %.

The catalyst bed is comprised of a catalyst on a support. The catalyst is any metal suitable for the oxidation of hydrogen dissolved in water to hydrogen peroxide. Materials suitable for the catalyst include, but are not limited to, platinum (Pt), palladium (Pd), ruthenium (Ru), rhodium (Rh), iridium (Ir), osmium (Os), gold (Au), and mixtures thereof. Preferably the catalyst material is selected from platinum, palladium, and a mixture thereof. The catalyst while consisting of a mixture of the aforementioned metals, can also include a mixture of iron and one of the aforementioned metals.

The catalyst material is deposited on a support. The support is any appropriate inert porous material for providing sufficient by large wettable surface area for the oxidation of hydrogen. Materials suitable for the support include, but are not limited to, carbon, carbon in the form of charcoal, silica, alumina, titania, zirconia, silicon carbide, hydrous silicic acid, silica-alumina, diatomaceous earth, clay, molecular sieves, polymers such as polyethylene, polypropylene, polystyrene, polytetrafluoroethylene, also known as TEFLON™, or a TEFLON related polymer, and mixtures thereof. Molecular sieves suitable for catalysts include, but are not limited to, zeolites such as H-ZSM-5 having a silica to alumina ratio of 6, and H-ferrierite having a silica to alumina ratio of 3.25. A preferable support is carbon.

In an alternative, the reactor is a fixed bed reactor wherein the fixed bed is an inert porous support with a catalyst. The fixed bed reactor is filled with water and the hydrogen and oxygen gases are bubbled through the reactor. The gases are preferably mixed, and dissolve in the water. The hydrogen is oxygenated in the aqueous phase forming a hydrogen peroxide solution. The solution is drawn off the reactor through a reactor outlet port.

The reactor design can be a concurrent flow reactor, as in the trickle bed, wherein the gas mixture flows in the same general direction as the water stream, or the design can be a countercurrent flow wherein the gas mixture bubbles upward against a downward flow of the water stream.

Other reactor alternatives include non-fixed bed reactors. An example of a non-fixed bed reactor includes a stirred tank reactor, either using a continuous or batch process. The stirred tank reactor includes a water inlet port in fluid communication with a reaction chamber for admitting water to the chamber. The reaction chamber comprises a reservoir for holding a catalyst on a support in a slurry comprising an aqueous solution and the catalyst on a support. The slurry is stirred with an impeller to mix the slurry keeping the solution well mixed with the catalyst. A gas inlet port is in fluid communication with the chamber for admitting the gas to the chamber. The gas inlet port can force the gas mixture into the solution through a sparger for creating a dispersion of small gas bubbles, or any other appropriate mechanism for distributing the gas in the solution. An aqueous solution of hydrogen peroxide is drawn from the reaction chamber through a product outlet port. The stirred tank reactor includes a screen positioned across the product outlet port for filtering the solid catalyst particles and preventing the catalyst particles from being swept out of the reaction chamber with the product solution. An alternative design can include a separation unit for separating the solid catalyst particles from the solution, and reinjecting the catalyst particles into the reaction chamber.

In the case of a carbon substrate, the catalyst bed is prepared by creating a porous carbon substrate, the substrate can be created by pyrolysis of heavy hydrocarbons, polymers, etc. The metal catalyst is deposited on the carbon substrate by processes known to those skilled in the art. Typical techniques are chemical vapor deposition, impregnation, etc. and are well known in the art.

For a catalyst comprised of a Pt and/or Pd metal on a silica or inorganic metal oxide support, the catalyst is prepared by spray-drying a mixture of a colloidal support material and a salt of the Pt and/or Pd metal. A preferred atomic ratio of Pt:Pd is from 0.01 to 0.1 with a more preferred ratio of about 0.05.

An alternate method of preparing the catalyst is by mixing silica with a concentrated solution of metal salts forming a paste. The paste is filtered and dried under conditions supporting a slow crystallization. The conditions include a reducing environment under hydrogen at a temperature between about 250° C. and about 400° C. The paste is treated with an acidic solution containing a bromide compound in a concentration from about 2 mg/l to about 20 mg/l, and bromine at a concentration from about 0.05 to about 2% by weight, and is treated at a temperature from about 10° C. to about 80° C. The paste is subsequently filtered and dried at a temperature from about 100° C. to about 140° C.

While the invention has been described with what are presently considered the preferred embodiments, it is to be understood that the invention is not limited to the disclosed embodiments, but is intended to cover various modifications and equivalent arrangements included with the scope of the appended claims.

What is claimed is:

1. A process for generating hydrogen peroxide directly from hydrogen and oxygen comprising:
    electrolyzing water into separate hydrogen ($H_2$) and oxygen ($O_2$) components;
    mixing the hydrogen and the oxygen in a micromixer to form a mixture; and
    reacting the mixture in a reactor under reaction condition to form hydrogen peroxide ($H_2O_2$).

2. The process of claim 1 further comprising the step of adding supplemental oxygen to the hydrogen and oxygen in the micromixer.

3. The process of claim 1 further comprising the step of adding air to the hydrogen and oxygen in the micromixer.

4. The process of claim 1 further comprising the step of splitting the hydrogen after the electrolyzing step into two streams and mixing one of the hydrogen streams with the oxygen in the mixing step.

5. The process of claim 4 wherein the oxygen ($O_2$) to hydrogen ($H_2$) molar ratio is between about 0.1 and about 10.

6. The process of claim 5 wherein the oxygen to hydrogen molar ratio is between about 2 and about 4.

7. The process of claim 1 wherein the reactor comprises a solid catalyst in an aqueous solution.

8. The process of claim 1 wherein the reactor is operated at a temperature between about 0° C. and about 60° C.

9. The process of claim 8 wherein the reactor is operated at a temperature between about 25° C. and about 40° C.

10. The process of claim 1 wherein the reactor is operated at a pressure between about 100 kPa and about 600 kPa.

11. The process of claim 1 wherein the reactor forms a solution of less than 5 mol % of $H_2O_2$ in water.

* * * * *